United States Patent [19]

Mason et al.

[11] Patent Number: 4,481,680
[45] Date of Patent: Nov. 13, 1984

[54] PROTECTIVE VISOR

[76] Inventors: Rosetta Mason, 2921 S. Western Ave., Los Angeles, Calif. 90018; Ruthie J. Crowe, 621 W. 62nd St., Los Angeles, Calif. 90044

[21] Appl. No.: 496,610

[22] Filed: May 20, 1983

[51] Int. Cl.³ .......................................... A42B 00/00
[52] U.S. Cl. ....................................... 2/174; 2/171.2; 2/181; 2/182.5; 2/DIG. 6
[58] Field of Search .............. 2/174, DIG. 6, DIG. 5, 2/171.2, 182.5, 181, 181.8

[56] References Cited

U.S. PATENT DOCUMENTS

| | | | |
|---|---|---|---|
| 2,032,898 | 4/1936 | Wilson | 2/174 |
| 2,143,265 | 7/1939 | Goldstein | 2/185 R |
| 3,529,308 | 4/1969 | McBride | 2/174 |
| 4,368,545 | 1/1983 | Seidman | 2/174 |

Primary Examiner—Werner H. Schroeder
Assistant Examiner—Mary A. Ellis
Attorney, Agent, or Firm—Spensley, Horn, Jubas & Lubitz

[57] ABSTRACT

A flexible, crescent-shaped planar strip is supplied with a raised rib along its inner concave edge. The raised rib is wrapped around the circumference of the user's head and the ends of the crescent-shaped strip are fastened together. Gutters of various dimension may be formed by manipulation of the flexible strip.

1 Claim, 5 Drawing Figures

PROTECTIVE VISOR

BACKGROUND OF THE INVENTION

1. Field of the Invention

The present invention relates to a protective visor and more particularly to a protective visor which creates a liquid impermeble barrier between the scalp and face or neck of the wearer.

2. Description of the Prior Art

Various hair and scalp treatments may involve the use of certain liquids and other substances which can cause extreme irritation if applied to the exposed face or neck of the user. Such treatments therefore require the use of some protective means to prevent the application of these substances to the user's face and neck.

In the past a number of devices have been suggested to overcome these problems. For example, U.S. Pat. No. 2,032,898 to Wilson discloses a soap guard which prevents soapy water from dripping into the eyes of the user. Such a device merely diverts the soapy water away from the eyes to an area behind the ears and down the back of the neck of the wearer. It is therefore unsuitable for use in conjunction with some of the more irritant liquids used in certain hair and scalp treatments. In addition, the gutter formed in such a device is fixed in both shape and dimension. This not only restricts the number of uses to which the device may be put, but also hinders the removal of any residue which may collect in the trough of the gutter.

An objective of the present invention is to provide a simple, inexpensive and practical protective visor which may be used to prevent liquid or other materials from dripping onto any portion of the user's face or neck.

A further objective of the present invention is to provide such a protective visor which is sufficiently flexible to allow the user to fashion a gutter of variable dimension.

SUMMARY OF THE INVENTION

In accordance with the present invention, these and other objectives are achieved by providing a planer strip of flexible material having a substantially crescent shape. A raised rib is provided along the inner edge of the crescent-shaped strip.

In operation, the raised rib is fitted securely around the circumference of the wearer's head and the ends of the crescent shaped strip are fastened together. A gutter of variable dimension may then be fashioned by turning up the flexible sides of the strip.

BRIEF DESCRIPTION OF THE DRAWINGS

A detailed description of the invention will be made with reference to the accompanying drawings, wherein like numerals designate corresponding parts in the several figures.

DESCRIPTION OF THE PREFERRED EMBODIMENT

The following detailed description is of the best presently contemplated mode of carrying out the invention. This description is not to be taken in a limiting sense, but is made merely for the purpose of illustrating the general principles of the invention. The scope of the invention is best defined by the appended claims.

Figure 1:
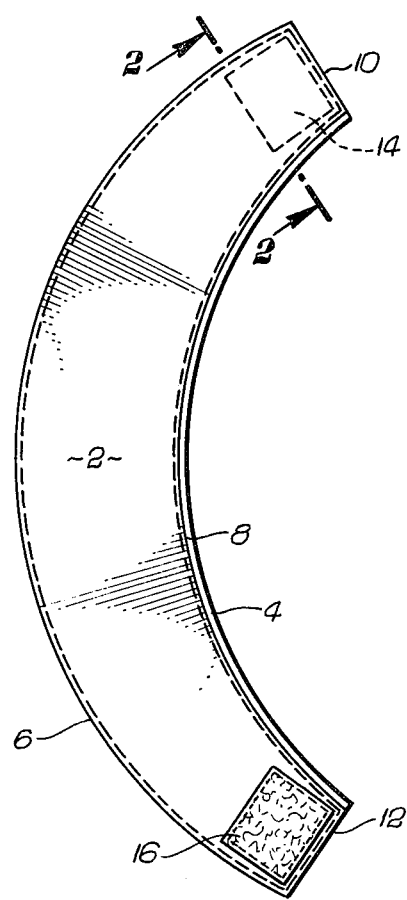
FIG. 1 is a view of a multi-purpose protective visor constructed in accordance with an embodiment of the present invention.
Figure 2:
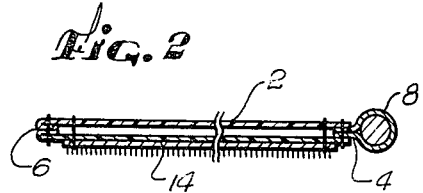
FIG. 2 is a somewhat exaggerated view in vertical section through the central portion of the visor shown in FIG. 1.

Referring to FIGS. 1 and 2, the protective visor consists of a planar strip 2 of flexible material having a substantially crescent shape. This crescent shape is defined on one side by a concave inner edge 4 and on the other side by a convex outer edge 6. In the present embodiment of the invention the strip 2 is composed of vinyl.

As shown most clearly in FIG. 2, a raised rib 8 is provided along the inner edge 4 of the strip 2. This raised rib 8 provides for a secure fit around the head of the user when the visor 2 is in use. In the preferred embodiment the raised rib 8 is formed by inserting a length of rope (not illustrated) into the inner edge 4 of the flexible strip 2.

The first end 10 and the second end 12 of the visor 2 are provided respectively with fastening means 14 and 16. In the preferred embodiment these fastening means consist of small rectangular patches of Velcro material. In operation, these fastening means 14 and 16 are joined together so that the raised rib 8 of the inner edge 4 of the protective visor 2 is secured firmly against the head of the user.

In operation, the inner edge 4 of the strip 2 is placed around the circumference of the head of the user. The ends 10 and 12 of the strip 2 are then pulled together tightly at the back of the user's head. The raised rib 8 is thereby pressed securely against the circumference of the user's head, creating a liquid impermeable barrier between the user's scalp and the user's face and neck.

The ends 10 and 12, which overlap to some degree behind the head of the user, are then joined together by fastening means 14 and 16. The strip 2 is thereby secured in place. It will be seen that due to the continuously adjustable nature of the fastening means 14 and 16 used in the preferred embodiment of the present invention, the same size strip 2 may be securely fitted to heads having a varying range of shapes and sizes.

Figure 3:
FIG. 3 is a view in side elevation illustrating the protective visor in a first operative position on the head of the wearer.

FIG. 3 illustrates the use of the visor 2 in a first mode of operation. In this mode any liquid or other material which is desired to kept off the face and neck of the user is dispersed evenly down the sides of the visor.

Figure 4:
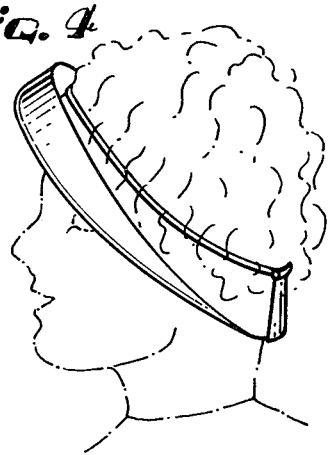
FIG. 4 is a view in side elevation illustrating the protective visor in a second operative position.

In a seocnd mode of operation illustrated in FIG. 4, the front portion of the flexible visor has been turned up to form a gutter across the forehead of the user. Liquid or other material will therefore be directed away from the forehead and eyes of the user and drained out the back of the visor.

Figure 5:
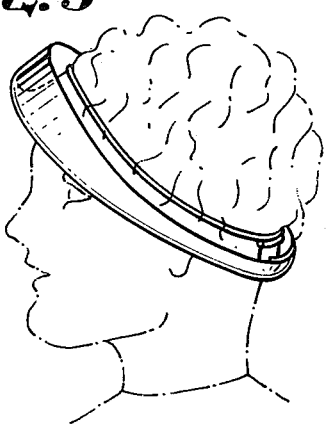
FIG. 5 is a view in side elevation illustrating the protective visor in a third operative position.

A third mode of operation is illustrated in FIG. 5. In this mode the flexible visor 2 has been turned up to form a gutter which completely encircles the head of the user. This circumferential gutter thereby collects all liquid or other material and the users face and neck are entirely protected.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A multi-purpose protective visor adapted to be positioned around the head of the user, said visor comprising:

a strip of foldable material having first and second opposed arcuate sides, the second arcuate side defining an inner edge of the strip, the strip being substantially crescent shaped;

the inner edge of said strip having a raised rib;

the ends of said strip being joined together so that said raised rib is securely pressed against the head of the user, wherein the strip is folded so as to form a gutter between at least a portion of the first arcuate side and at least a portion of the second arcuate side, the gutter extending across at least a portion of the head of the user.

* * * * *